United States Patent
Pierce et al.

[19]

[11] Patent Number: 5,871,353
[45] Date of Patent: Feb. 16, 1999

[54] PROPHY ANGLES WITH DENTIFRICE DISPENSING SYSTEMS

[76] Inventors: James E. Pierce, 6497 La Cumbre, Somis, Calif. 93066; Sten Lagerstadt, Åloppev 12, S-16856 Bromma, Sweden

[21] Appl. No.: 798,882

[22] Filed: Feb. 11, 1997

Related U.S. Application Data

[60] Provisional application No. 60/011,460 Feb. 12, 1996.
[51] Int. Cl.⁶ .................................................. A61C 1/10
[52] U.S. Cl. .............................. 433/84; 433/83; 433/125; 433/166
[58] Field of Search ............................... 433/82, 125, 83, 433/84, 85, 87, 89, 114, 166

[56] References Cited

U.S. PATENT DOCUMENTS

| | | | |
|---|---|---|---|
| 2,400,912 | 5/1946 | Britt et al. | 433/82 |
| 2,738,528 | 3/1956 | Fridge, Sr. | 433/82 |
| 3,389,468 | 6/1968 | Lewis et al. | 433/82 |
| 3,579,835 | 5/1971 | Levenson | 433/82 |
| 4,014,100 | 3/1977 | Spotteck | 433/84 |
| 4,097,995 | 7/1978 | Danne et al. | 433/82 |
| 4,220,446 | 9/1980 | Walker | 433/88 |
| 4,266,933 | 5/1981 | Warden et al. | 433/82 |
| 5,062,796 | 11/1991 | Rosenberg | 433/82 |
| 5,642,994 | 7/1997 | Chipian et al. | 433/82 |
| 5,692,901 | 12/1997 | Roth et al. | 433/85 |

*Primary Examiner*—Ralph A. Lewis
*Attorney, Agent, or Firm*—Kenneth J. Hovet

[57] ABSTRACT

The invention provides for the incorporation of dentifrice preparations, which are commonly accessed from a container on a tray during teeth cleaning, internally within the housing of a disposable prophy angle. Auger, baffle or piston members are used to move the preparations from the housing through passages in the head of the prophy angle to a moving prophy cup. If a reusable autoclavable prophy angle is being used, the invention provides for an annular chamber containing the dentifrice preparation that interfits as a sleeve over the prophy angle body. In such case, the prophy angle head is enlarged and includes an inlet connection with the annular chamber. Passageways in the head direct the dentifrice preparation to the prophy cup and a piston ring is used to move the dentifrice preparation from the chamber through the passageways. Alternatively, an external pressurized supply of the dentifrice preparation may be connected to a conduit which is attached to the body in place of the annular chamber. The conduit interconnects the external supply with the enlarged head inlet for providing dentifrice preparation to the prophy cup. In all cases, the prophy cup may include a one-way valve to prevent backflow of unwanted materials.

8 Claims, 7 Drawing Sheets

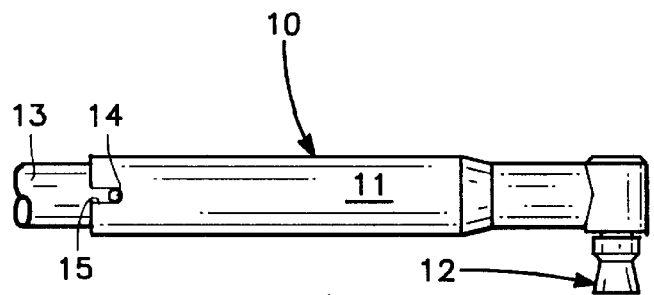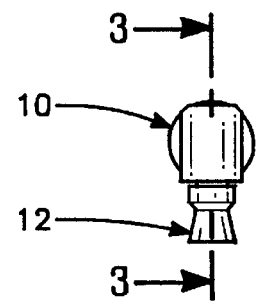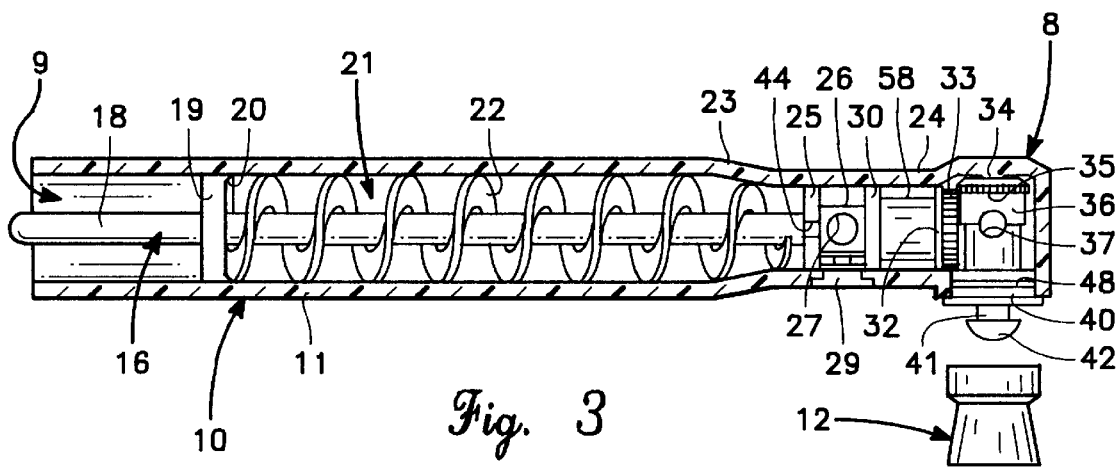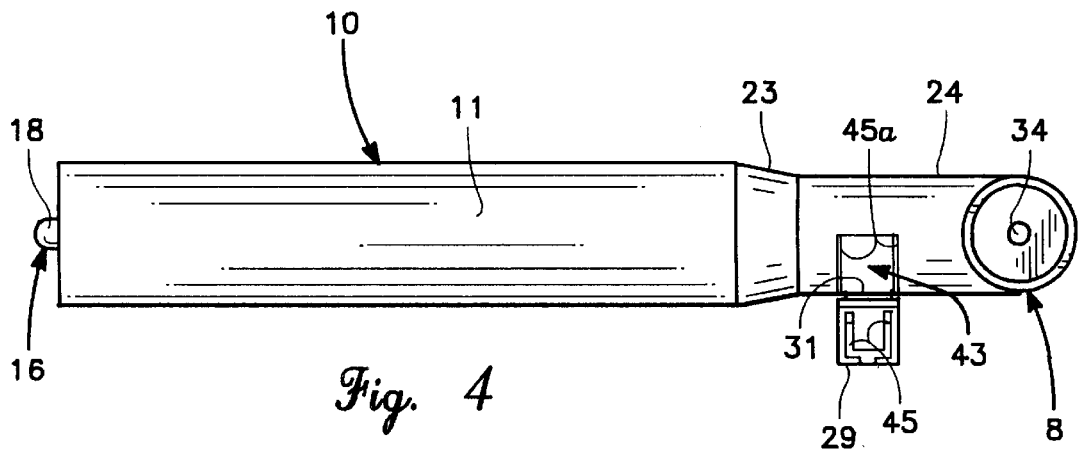

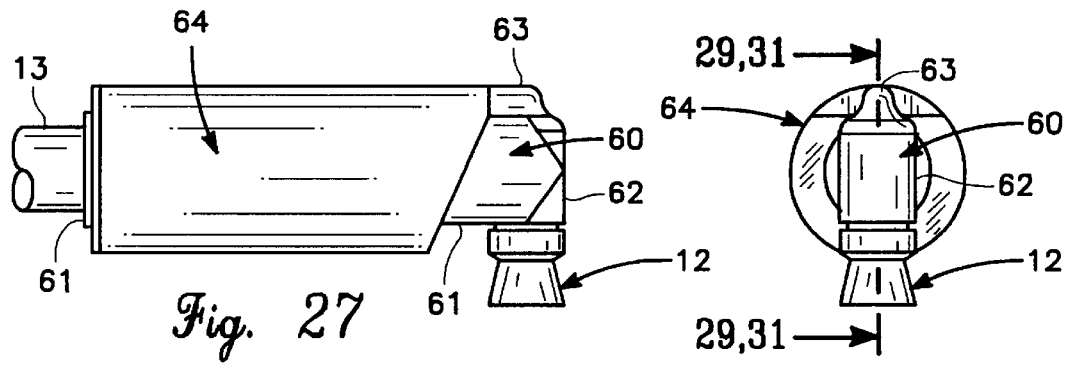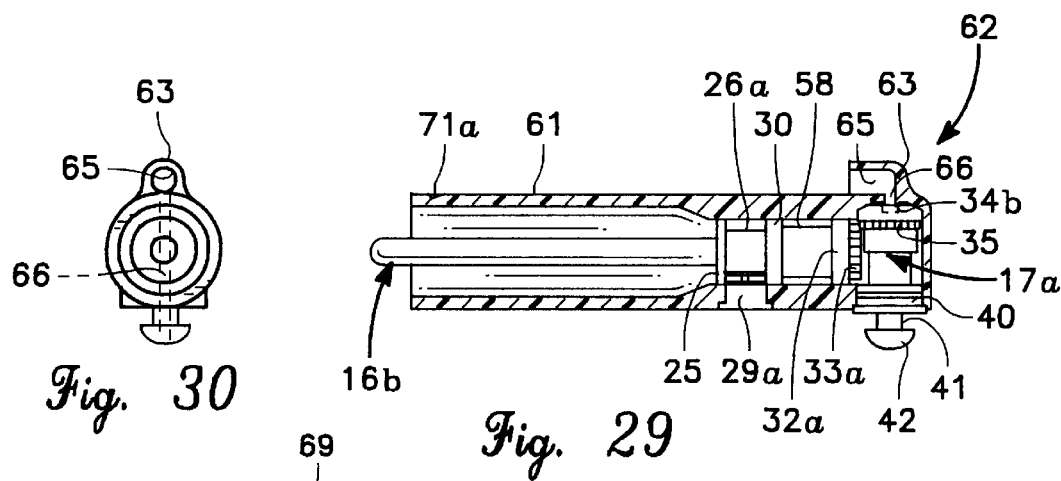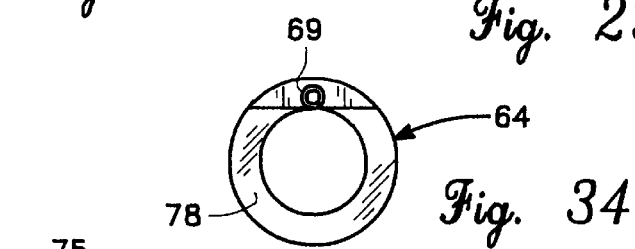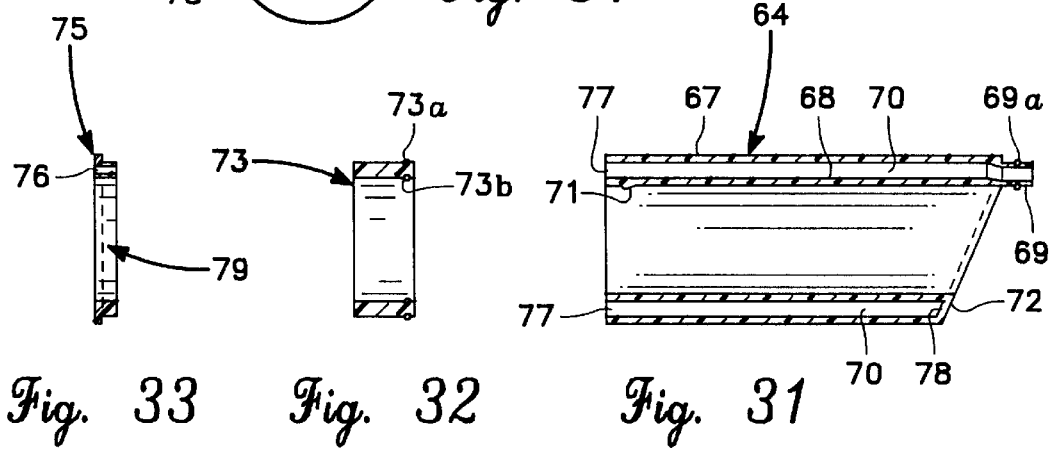

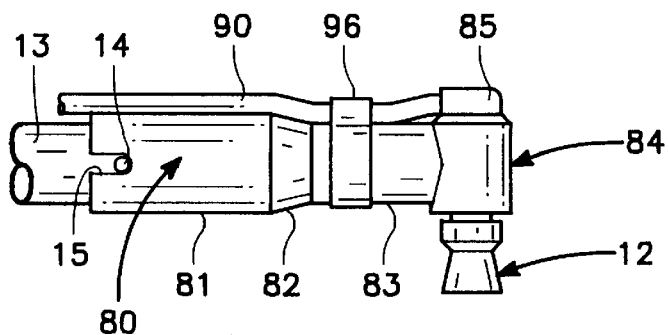
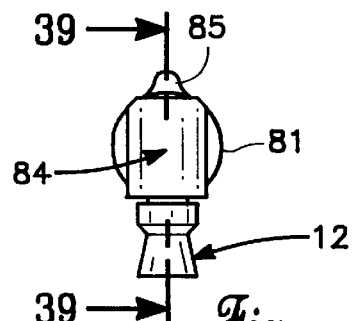
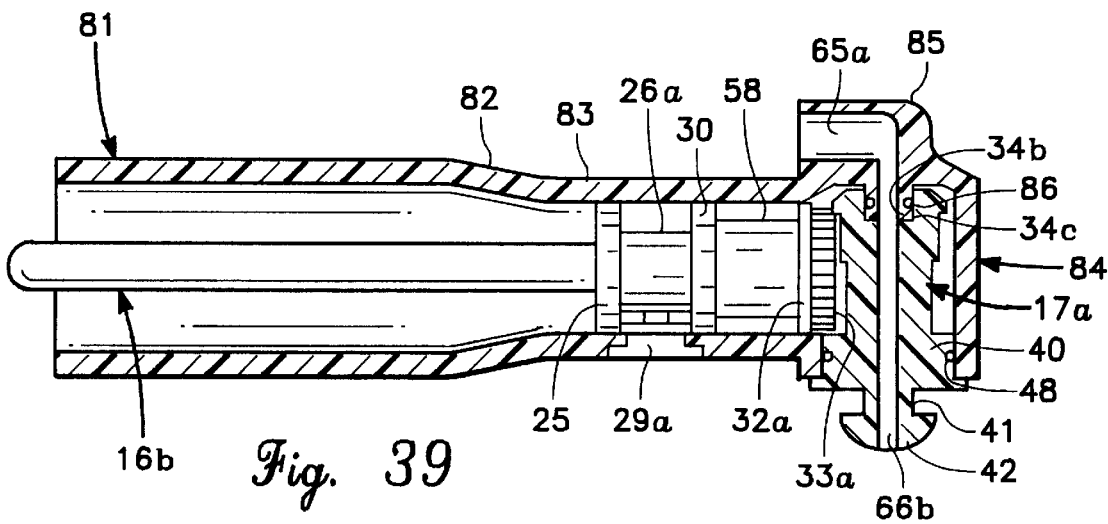
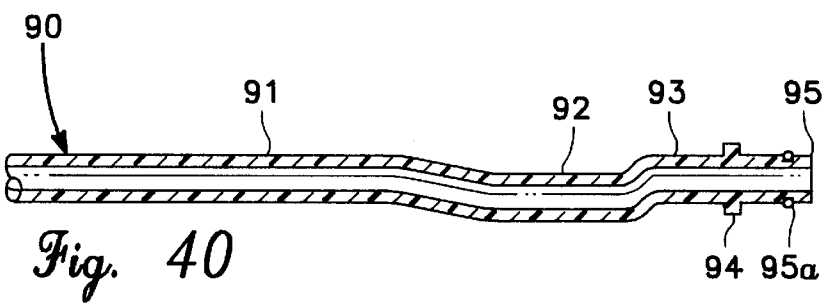
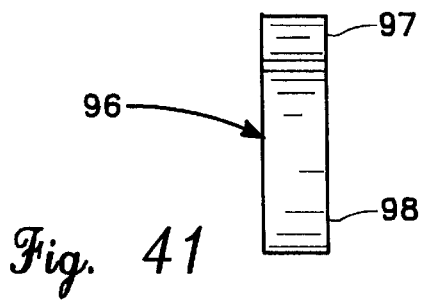
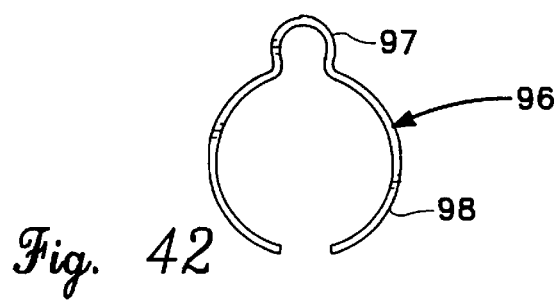

PROPHY ANGLES WITH DENTIFRICE DISPENSING SYSTEMS

BACKGROUND OF THE INVENTION

This application claims priority from Provisional Patent Application No. 60/011,460, filed on Feb. 12, 1996.

1. Field of the Invention

The invention relates, generally, to improvements in implements wherein a moving tool part utilizes a flowable material for cleaning, bleaching, polishing or abrading a workpiece. More particularly, it relates to incorporation of dentifrice dispensing systems into disposable prophy angles. It also relates to the incorporation of dentifrice dispensing means with reusable prophy angles.

2. Description of Related Art

Heretofore, two general types of prophy angles (i.e., dental prophylaxis right angle hand pieces) have been available. One type is a relatively expensive reusable type formed of metal parts suitable for repeated usage and requiring sterilization after each use. Another general type is formed of plastics and is disposable after one time use.

In recent years, concern has increased for preventing the transmission of diseases during dental procedures. Disposable prophy angles were conceived in an attempt to prevent spread of disease from patient to patient. Some disposable prophy angles incorporate blocking devices to prevent migration of buccal matter from the patient's mouth back through the prophy angle to the dentist's handset thus also protecting the operator. An example of such device is shown in U.S. Pat. No. 5,209,658 to Brahler. This device uses sealing rings to block buccal matter and auger flights to propel such matter from the head end.

Both of the above prophy angles include a prophy cup for receiving dentifrice preparations and applying the preparations to a patient's teeth. To accomplish this, the cup is dipped into a container of dentifrice material which is usually located on a tray a few feet from the patient. Once the cup is filled, it is then transported to the patient's mouth to continue prophylaxis. Typically, the dentifrice material is dissipated fairly quickly. To completely clean a patient's teeth, it is necessary to repeat the above steps numerous times. Applicant is unaware of any prophy angle that will avoid the above sequence of time consuming cumbersome steps.

SUMMARY OF THE INVENTION

An object of this invention is to provide a continuous supply of flowable material directly to the moving tool part by providing dispensing systems that are integral with the implement.

With particular respect to dentistry, another object of the invention is to provide barriers against migration of buccal matter from the patient's mouth that may contaminate a dental hand piece.

These and other objects of the invention are attained by incorporating dispensing systems proximate to the implement whereby operator-controlled flowable material will be dispensed directly to the moving tool part for continuous cleaning, polishing, bleaching or abrading work. Particular utility is found in the dental art wherein the storage and dispensation of dentifrice preparation is incorporated into reusable and disposable prophy angles.

In accordance with the invention, an implement housing having a dispensing head from which extends a movable tool part is provided wherein the dispensing head includes an extension having an inlet passage in communication with a supply of flowable material. The dispensing head includes a head gear unit and includes an aperture in communication with the tool part and inlet passage for permitting flow of material to the tool part.

To actuate the gear unit, a drive shaft is provided that extends through the body to an external power source. In some cases, the body itself may define a storage area or otherwise may create a chamber for containing the flowable material. In such case, the body includes a displacement means for moving the material from the supply means through predetermined apertures or passageways to the tool part. The displacement means may be connected to the drive shaft for effecting movement of the flowable material. Examples of this are inclined paddles and spiral baffles.

Alternatively, the displacement means may utilize a piston member which may have a manual actuating means such as a knob which can be moved with an operator's thumb during operation of the implement. The piston member may also be driven by pneumatic, hydraulic or electromechanical means known in the art.

With respect to the application of the invention in the field of dentistry, wherein the dentist's hand piece is not disposable, the invention contemplates an elongated annular dentifrice chamber that serves as a sleeve to surround a portion of the body of the dentist's prophy angle. In this case, the annular chamber would include a fitting for connection to an enlarged dispensing head. The head will include passageways for flowing the dentifrice to the spinning prophy cup.

In one embodiment of the invention, a source of dentifrice preparation is pre-installed internal to the disposable prophy angle. In a first alternative to this embodiment, transport means for moving such preparation comprises spiral baffles attached to the internal drive shaft. The baffles convey the preparation to a dispensing head enclosing a gear train. Passages in the head or through the gear train direct the dentifrice to the prophy cup. The cup may include a one-way valve in the base of the cup. In a second alternative, the transport means comprises an internal piston that extrudes the preparation, upon operator demand, through the passages into the prophy cup.

In another embodiment of the invention, the source of dentifrice preparation is located external and proximate to a reusable prophy angle. In a first alternative to this embodiment, an annular chamber with internal piston actuation is used as a dentifrice storage and transport means. In a second alternative, a dentifrice supply means, located apart from the reusable prophy angle, is used for flowing the dentifrice preparation to the dispensing head of the prophy angle body. The object of this alternative is to provide a reduced profile for the reusable prophy angle so that it will be more comfortable to the patient during prophylaxis.

BRIEF DESCRIPTION OF THE DRAWINGS

Two illustrative embodiments, each having two alternatives, are shown in the appended drawings.

First Alternative to the First Embodiment

FIG. 1 is a side elevation view of a disposable prophy angle in which dentifrice preparation is dispensed from an internal supply.

FIG. 2 is a right end elevation view of the prophy angle shown in FIG. 1.

FIG. 3 is an enlarged one-half section view taken along line 3—3 of FIG. 2 showing a drive shaft with dispensing auger and gear in communication with a right angle gear shaft including a prophy cup spaced-apart therefrom.

FIG. 4 is a bottom plan view of the housing shown in FIG. 3 illustrating a living hinge bearing retainer mechanism.

Second Alternative to the First Embodiment

Figure 18:
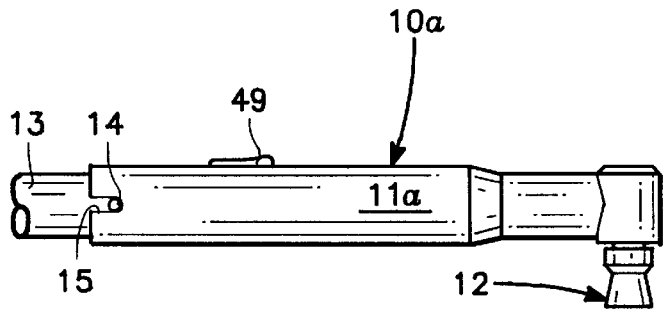

FIG. 18 is a side elevation view of a disposable prophy angle similar to that shown in FIG. 1 incorporating alternative transport means for manually moving dentifrice preparation from internal storage to the prophy cup.

Figure 19:
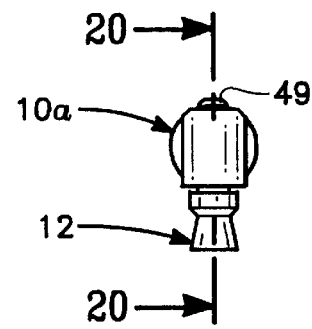

FIG. 19 is a right end elevation view of the prophy angle shown in FIG. 18.

Figure 20:
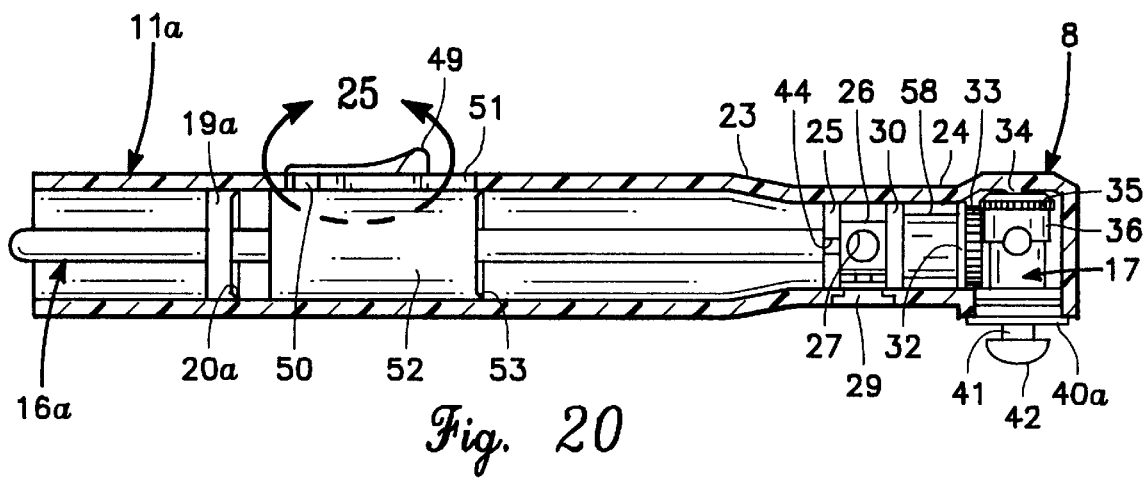

FIG. 20 is an enlarged one-half section view taken along line 20—20 of FIG. 19 showing a drive shaft rotating within a dentifrice dispensing piston and rear seal bearing, the shaft including the previously shown bearings and drive gear in communication with a right angle gear unit.

Figure 21:
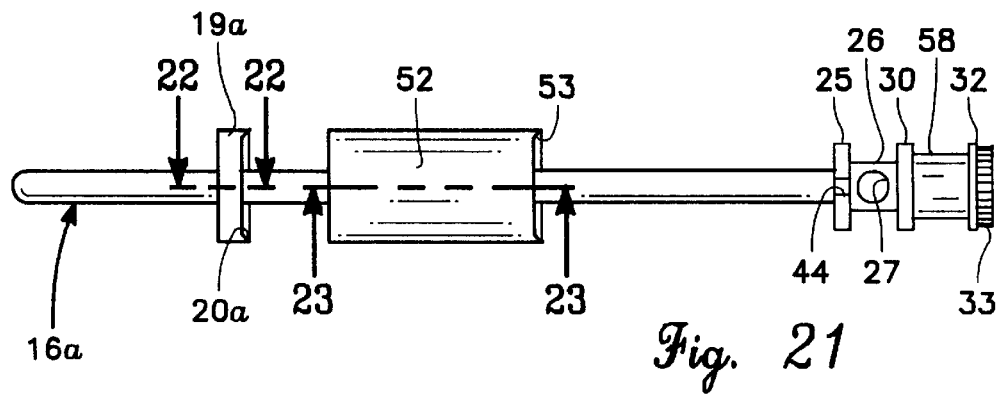

FIG. 21 is a side elevation view of the drive shaft, bearings, drive gear, piston and rear seal bearing shown in FIG. 20.

Figures 22, 23, 24:
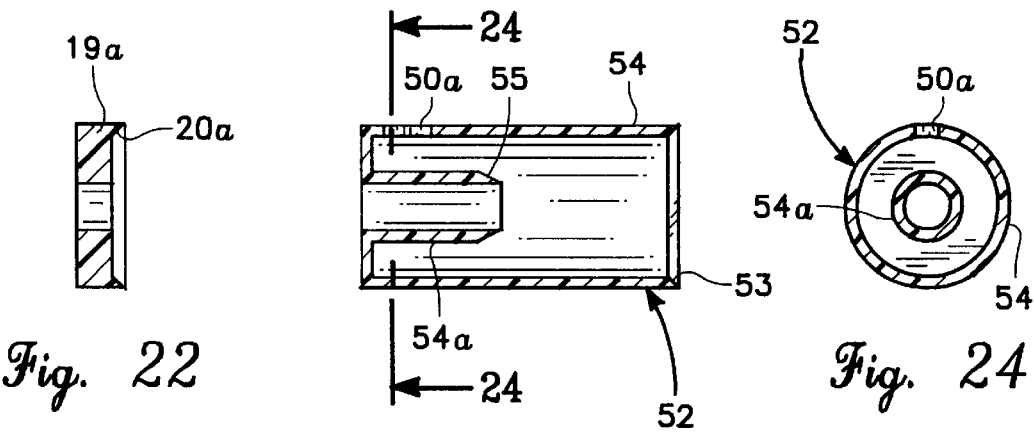

FIG. 22 is a cross-sectional view taken along line 22—22 of FIG. 21 showing the rear seal bearing.

FIG. 23 is a cross-sectional view of the piston taken along line 23—23 of FIG. 21.

FIG. 24 is a right end elevation view of the piston shown in FIG. 23.

Figures 25, 26:
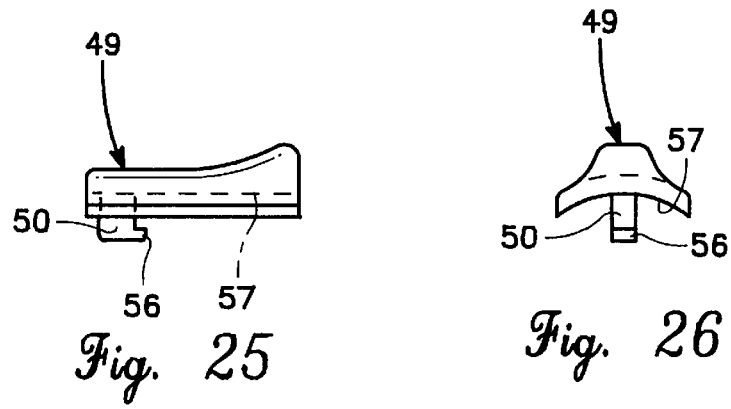

FIG. 25 is a side elevation view of the piston control knob shown in FIG. 20.

FIG. 26 is a right end elevation view of the control knob shown in FIG. 25.

First Alternative to the Second Embodiment

FIG. 27 is a side elevation view of a reusable prophy angle modified for attachment of a disposable cylindrical dentifrice dispenser chamber.

FIG. 28 is a right end elevation view of the prophy angle shown in FIG. 27.

FIG. 29 is a one-half section view taken along line 29—29 of FIG. 28 showing modifications to the reusable prophy angle body and gear train without the dispenser chamber and its related parts.

FIG. 30 is a left end elevation view of the reusable prophy angle shown in FIG. 29.

FIG. 31 is a side cross-sectional view taken along line 31—31 of FIG. 28 showing the dispenser chamber without the modified body and drive assembly shown in FIG. 29.

FIG. 32 is a cross-sectional view of a piston ring in position for assembly into the dispenser chamber of FIG. 31.

FIG. 33 is a cross-sectional view of a cap ring in position to fit into and seal the open end of the dispenser chamber of FIG. 31.

FIG. 34 is a right end elevation view of the dispenser chamber shown in FIG. 31.

Figures 35, 36:
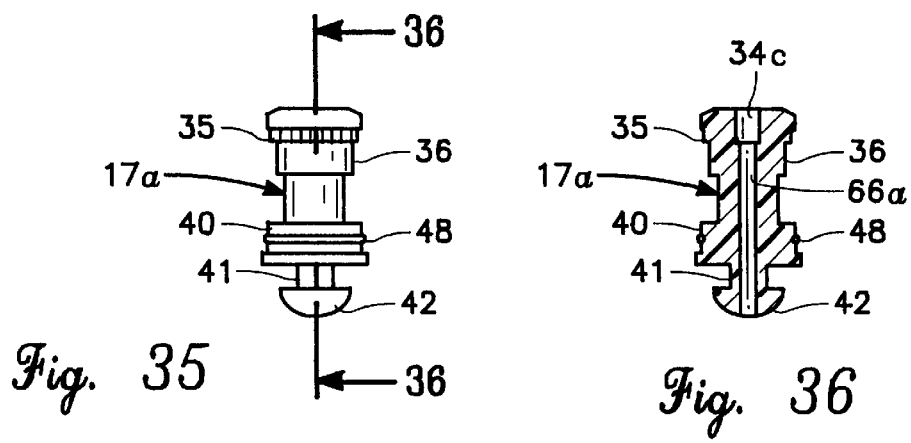

FIG. 35 is a side elevation view of the modified right angle gear unit shown in FIG. 29.

FIG. 36 is a cross-sectional view taken along line 36—36 of FIG. 35 showing axial passageways in the modified right angle gear unit.

Second Alternative to the Second Embodiment

FIG. 37 is a side elevation view of a reusable prophy angle modified for attachment of a disposable dentifrice conduit.

FIG. 38 is a right end elevation view of the reusable prophy angle shown in FIG. 37.

FIG. 39 is an enlarged one-half section view taken along line 39—39 of FIG. 38 showing modifications to the prophy body and the right angle drive unit.

FIG. 40 is an enlarged side cross-sectional view of the conduit illustrated in FIG. 37.

FIG. 41 is a side elevation view of a fastener used to secure the conduit to the body of the prophy angle as shown in FIG. 37.

FIG. 42 is a right end elevation view of the fastener shown in FIG. 41.

DESCRIPTION OF THE PREFERRED EMBODIMENTS

First Embodiment: Disposable Prophy Angles for Dispensing Dentifrice
First Alternative: Auger Conveyance System In FIG. 1, a disposable prophy angle is indicated generally at 10. In this version of the first embodiment, a disposable prophy angle is assembled from three component parts: A housing 11 through which extends a drive shaft 16 having a drive gear section engaged with a right angle gear unit 17. A conventional prophy cup 12, which may be modified to include a one-way valve, is attached after assembly is completed. The prophy angle is attached to a standard rotatable sheath-and-lock-collet dental hand piece 13 by inserting the free end 18 of the drive shaft into the collet until sheath pin 14 engages slot 15 in the prophy angle housing.

Figure 5:
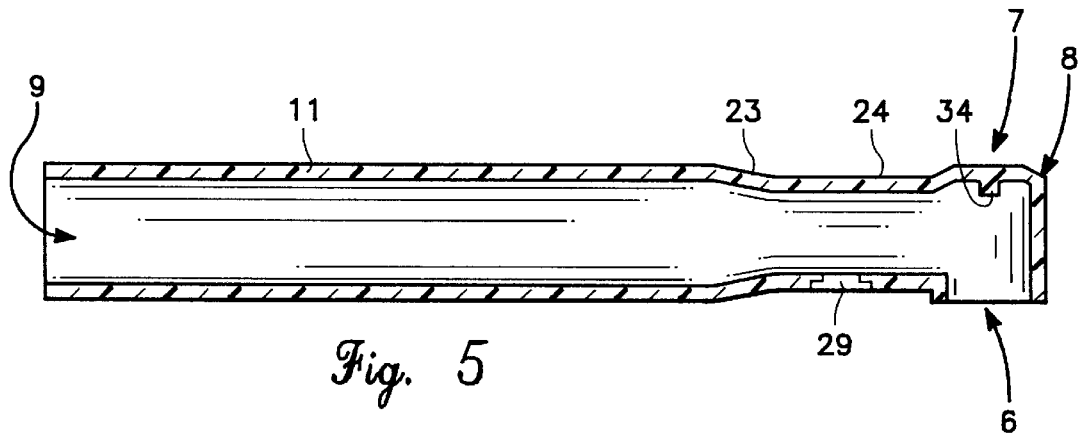
FIG. 5 is a side elevation view of the housing cross-section shown in FIG. 3 with working parts removed.

Housing 11, shown in FIGS. 3–5, is typically formed from plastic by injection molding processes, however, other processes such as resin casting could be used. The housing has a first open end 9 and an opposing second end 7. It is comprised of a tubular body section which merges into a tapered section 23 followed by a tubular bearing section 24 and an integrally molded dispensing head section 8. The body section has an internal diameter sized to slip fit over the sheath of a dental hand piece. The minor internal diameter of bearing section 24 is sized to provide a rotational bearing surface for auger drive shaft 16. The head section integrally incorporates housing extension pin 34 to provide a bearing surface and alignment for right angle gear unit 17.

Auger drive shaft 16, shown in FIG. 3 and FIGS. 6–9, is typically injection molded as a single unit from plastic. The drive shaft comprises several integrated sections. The rearward free end section 18 comprises a connector end for attachment to a standard sheath-and-lock-collet dental drive 13 as depicted in FIG. 1.

Spaced forward of free end section 18 is an integrally formed outer end bearing 19 and end seal 20 having an outside diameter sized to slip fit into the internal diameter of the tubular body portion of housing 11. End bearing 19 centers the auger drive shaft and provides a bearing surface for the shaft as it rotates. End seal 20 is typically a lip seal integrally formed on the bearing forward edge. It expands radially as pressure increases during dentifrice flow and seals against the inner walls of the tubular housing portion.

Figure 6:
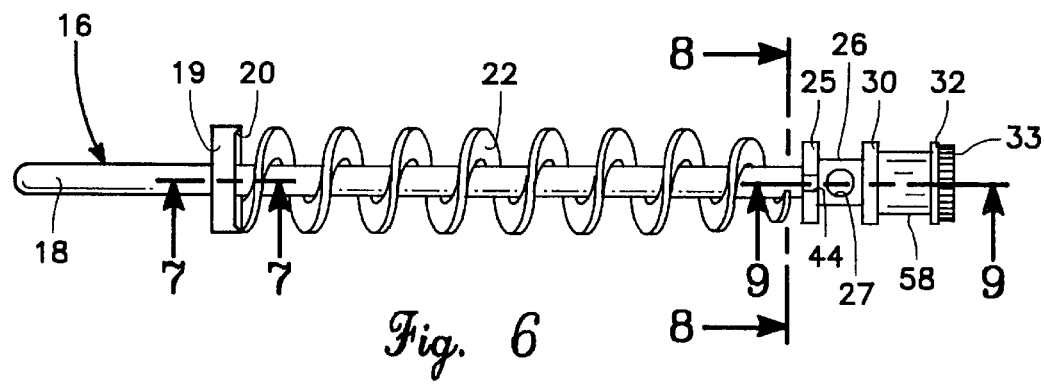
FIG. 6 is a side elevation view of the unitized drive shaft, auger, bearing section and drive gear which was shown in FIG. 3 within the housing.
Figure 7:
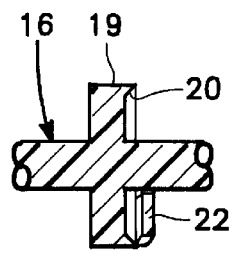
FIG. 7 is a side cross-sectional view taken along line 7—7 of FIG. 6 showing unitized construction of the drive shaft, rear bearing and seal, and auger flute attachment.

Spaced axially forward of the end bearing 19 is a transport section 21. As shown in FIGS. 3, 6 and 7, the transport section includes auger flutes 22 extending radially outward from the shaft in a spiral path. The auger flutes are offset from the shaft but are connected to opposing ends of the shaft transport section. The purpose of such offset is to provide space for dentifrice by-pass during rotation of the shaft. Also, the profile of the auger conveying surface cooperates with the size of orifice passages in the gear units and prophy cup to provide uniform continuous flow of dentifrice at specified rotational speeds.

Flutes having a left-hand spiral convey dentifrice forward into the dispensing head section of the prophy angle when the drive shaft is rotated clockwise in the assembly. Although a reduced profile auger is used herein for illustration, other by-passing continuous transport means are within the scope of this embodiment. Examples are inclined paddle structures, intermittent baffles or twisted and cork-screw shaped segments of the transport section.

Located axially forward of the auger drive section is a series of three spaced-apart rib bearings comprising inner bearing 25, mid-bearing 30 and gear bearing 32. Shaft drive section 26 separates inner bearing 25 from mid-bearing 30. Bearing shaft section 58 separates the mid-bearing from gear bearing 32. The gear bearing incorporates drive gear 33 on its outer face. The inner bearing 25, in cooperation with end bearing 19, function to axially center the drive shaft to the housing. The outside diameters of the bearings are sized to slip-fit into the internal diameter of bearing section 24 of the housing and to rotate therein.

As shown in FIGS. 3 and 4, a door 29 is attached to the housing during the molding process with a thin plastic "living hinge" 31. When the door is moved into door opening 43, male flanges 45 on the door inner face engage mating flanges 45a in the opening. This engagement provides an interference latching closure that also seals against internal pressure.

The door serves a dual purpose. When it is closed, the male flanges 45 protrude into the housing bearing section to a position proximate shaft section 26 between and against inner bearing 25 and mid-bearing 30. Thus, the door flanges position and retain the drive shaft in precise location within the housing. At the same time, drive gear 33 becomes engaged with spur gear 35 on right angle gear unit 17, as described hereinbelow, thereby also retaining that unit in its precise location upon assembly.

Figure 8:
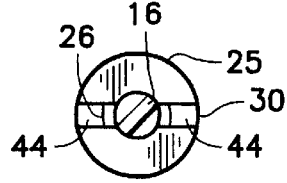
FIG. 8 is an axial cross-sectional view taken along line 8—8 of FIG. 6 showing access slots for dentifrice preparation flow in the forward bearing section of the shaft.
Figure 9:
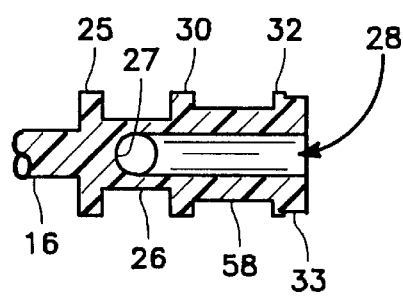
FIG. 9 is a side cross-sectional view taken along line 9—9 of FIG. 6 showing radial and axial holes in the forward bearing and shaft gear unit to facilitate dentifrice preparation flow.
Figure 12:
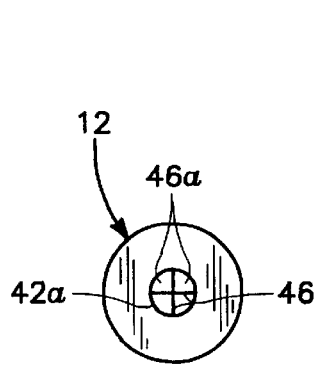
FIG. 12 is a top plan view of the prophy cup shown in FIG. 10.
Figure 11:
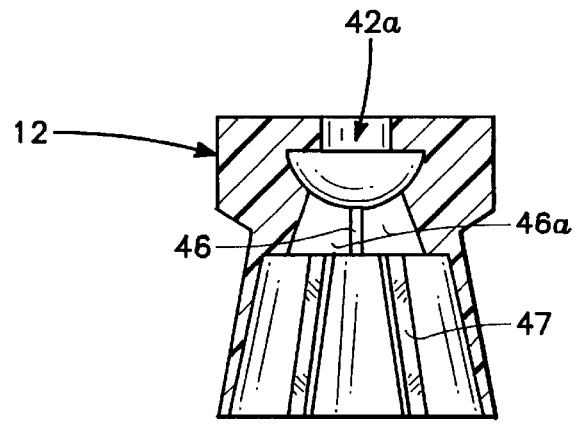
FIG. 11 is an enlarged cross-sectional view taken along line 11—11 of FIG. 10 illustrating the one-way check valve construction internal to the prophy cup.
Figure 10:
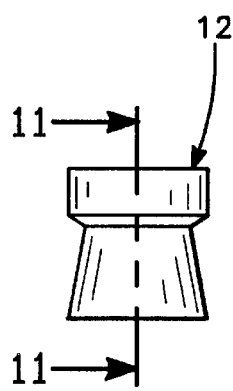
FIG. 10 is a side elevation of the prophy cup shown in FIG. 3.
Figure 14:
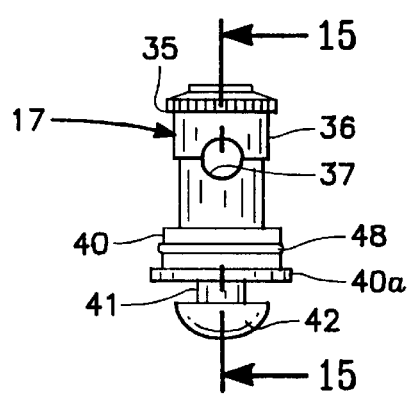
FIG. 14 is a side elevation view of the right angle gear unit shown in FIG. 3.
Figure 15:
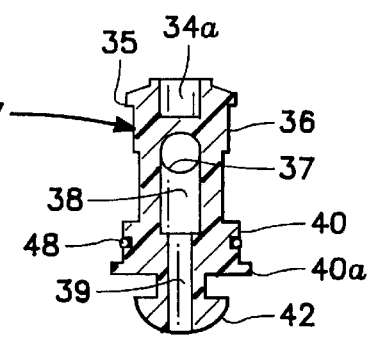
FIG. 15 is a cross-sectional view taken along line 15—15 of FIG. 14 showing radial and axial passages in the right angle gear unit to direct the flow of dentifrice preparation.
Figure 13:
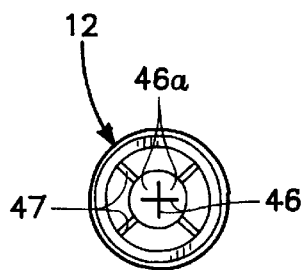
FIG. 13 is a bottom view of the prophy cup shown in FIG. 10.
Figure 16:
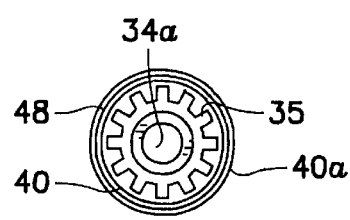
FIG. 16 is a top plan view of the right angle gear unit shown in FIG. 14.
Figure 17:
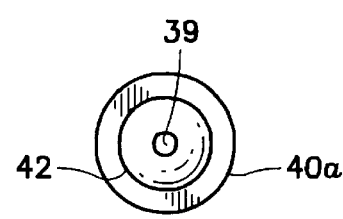
FIG. 17 is a bottom plan view of the right angle gear unit shown in FIG. 14.

The second purpose for door 29 is to provide a bleed port for excess air when dentifrice is being loaded into the assembly. As shown in FIG. 8, inner bearing 25 has two slots 44 that provide for passage of dentifrice into the shaft drive section 26. The drive section includes a radial opening 27 connecting to an axial aperture 28, as shown in FIG. 9. Dentifrice conveyed by the auger flutes passes through slots 44 into radial opening 27 and out through the axial aperture into the dispensing head section of the housing.

FIG. 3 and FIGS. 14–16 show the right angle gear drive unit 17. This unit is typically injection molded and includes spur gear 35 and internal bearing recess 34a at the top. The unit mid-portion includes a stepped shaft section 36 which extends into a lower bearing 40 having a lower seal 48. The unit bottom portion comprises post 41 from which extends button 42. The stepped shaft section has radial orifice 37 which intersects with stepped aperture 38. The stepped aperture extends through the button to outlet 39. Radial orifice 37 is aligned with the axial centerline of axial aperture 28 of shaft drive section 58. The center axes of stepped aperture 38 and outlet 39 are coextensive with the centerline of right angle gear unit 17.

During operation, dentifrice exiting axial aperture 28 in the drive shaft, flows into radial orifice 37 in the right angle drive unit. It then flows through stepped aperture 38 and outlet 39 into the prophy cup. Lower seal 48 prevents dentifrice from leaking into the dispensing head cavity.

Three alignment surfaces are incorporated into the right angle drive unit 17. It is aligned axially by housing extension pin 34 at the top shown in FIGS. 3 and 5 which mates with the bearing recess 34a. Alignment is also maintained at the bottom by external flange 40a of bearing 40. Unit 17 is further retained and locked in precise gear alignment by a center boss (not shown) on drive gear 33 which extends under spur gear 35 and bears on the larger diameter of stepped shaft section 36.

As shown in FIG. 3, post 41 and button 42 extend angularly downward about perpendicular to the housing longitudinal axis. Prophy cup 12 is mounted and retained on button 42 by the cup's elastic engagement with a button profiled cavity 42a in the cup upper body portion. A variety of standard commercially available prophy cups effectively seal on post 41 and button 42 and include cup outlets (not shown) for communicating with dentifrice flowing from button outlet 39 into the flared lower cup outlet area.

As shown in FIGS. 10–13, the standard cup has been modified by piercing axially through the lower portion of the cup body with a pronged piercing tool. This action produces slits 46 which extend through the cup bottom. Each slit is made at the same angle from the centerline axis of the cup. Included in the skirt are guide ribs 47 for effecting the even distribution of dentifrice. The intersecting slits 46 form elastic quadrant parts 46a in the cup bottom. When pushed by the flow of dentifrice, the quadrant parts will flex and slightly separate at the slit intersection. This will permit flow outwardly but not inwardly. As such, a one-way valve is created that prevents backward flow of either used dentifrice or buccal matter.

The above one-way valve is created via the inherent flexing characteristics of the rubber cup body. Other one-way valves such as flapper or ball check valves known in the industry could be used. Similarly, O-ring seals on some of the bearings are illustrative of effective seals useful in the present invention. Likewise, mechanical seals and matching gasket assemblies known in the sealing industry could also be used with the invention.

Upon assembly, right angle gear unit 17 is inserted into second end opening 6 of the housing and then drive shaft 16 is inserted until drive gear 33 is engaged with spur gear 35 of each respective drive section 26 and right angle drive unit 17. By closing and locking door 29, the precise positions of the drive shaft, drive section and angle drive unit are maintained. Prior to inserting the auger drive shaft, dentifrice is extruded into the first open end 9 of the housing with door 29 in its closed position. Such dentifrice flows around and into the apertures of right angle drive unit 17. Air is bled from button outlet 39 until dentifrice flows from the outlet. The outlet is then plugged and the remainder of housing 11 is filled.

After loading dentifrice and completing the assembly of parts, the filled prophy angle is preserved in a sealed, inert packaging environment that maintains shelf life of the dentifrice.

In use, the disposable prophy angle 10 is mounted in a conventional manner onto a standard dental drive sheath and lock collet as indicated at 13 in FIG. 1. Housing 11 is prevented from rotating by the engagement of sheath pin 14 in slot 15 of the housing. Connector end 18 of the drive shaft 16 is rotated clockwise from the collet connection of the dental tool which in turn rotates auger 22 and gear 33. Engagement between gears 33 and 35 induces clockwise rotation of right angle gear unit 17 and thus prophy cup 12. When auger flutes 22 rotate, pressure develops in the auger drive section 21. This pressure conveys dentifrice through passages in the drive section and right angle gear unit into prophy cup 12 as the path of least resistance. A sufficient quantity of dentifrice is loaded in the prophy angle for a complete prophylaxis procedure. When the procedure is complete, the entire prophy angle is safely discarded, thus obviating the need for sterilization and eliminating separate supplies of dental dentifrice. When the one-way valve is included in the prophy cup, migration of buccal matter, which may contain communicable disease to the dental hand piece, will be blocked.

Second Alternative: Piston Conveyance System

A second version of the first embodiment is illustrated in FIGS. 18–26. An inherent feature of an auger conveyance system is that dentifrice flow is somewhat dependent on rotational speed of the dental hand piece, auger construction, and passageway sizes. This second version provides operator control of dentifrice flow by employing a manual sliding piston to move dentifrice through the assembly into the prophy cup. Although a piston mechanism is illustrated, the invention is able to accommodate a variety of mechanisms and controls known in the art. Examples are squeeze tubes, pressure actuation and mechanical leverage devices.

The second version of a disposable prophy angle is indicated generally at 10a in FIG. 18 and is comprise of housing 11a, drive shaft 16a having an integral drive gear 33, rear bearing 19a, cup piston 52, and right angle drive unit 17.

Housing 11a is similar to auger housing 11. The only change is the addition of a longitudinal housing slot 51 through the top wall proximate the mid-length of the housing. Said slot provides access for attachment of knob 49 to the cup piston by means of tang 50. The slot accommodates the longitudinal stroke length of the piston. The tang extends through the slot and is secured to the outer cylinder 54 of the piston.

Drive shaft 16a is typically the same length as auger drive shaft 16, but does not include an integral rear bearing or auger portion. Thus, drive shaft 16a is a long uniform shaft terminated by the drive section 26. Right angle gear unit 17 and the prophy cup 12 are the same as in the auger alternative.

As shown in FIGS. 20–22, rear bearing 19a is a separate component from drive shaft 16a to facilitate installation of piston 52. After the piston is assembled over the drive shaft, the rear bearing is secured to the drive shaft in the position shown in FIGS. 20 and 21. The outside diameter of rear bearing 19a is sized to rotate inside housing 11a and to center shaft 16a and piston 52 in the housing. Peripheral lip seal 20a is incorporated onto the leading edge of bearing 19a and serves the same sealing function as described previously.

The cup piston has an outer cylinder 54 and an inner cylinder 54a and resembles an annular cup. Lengths of both cylinders are sized to prevent cocking either within the housing or on the drive shaft. Piston lip seals 53 and 55 are incorporated on the leading cylinder edges. The seals expand when pressure is applied and wipe both the housing and the drive shaft surfaces respectively to prevent backward flow of dentifrice. Note that peripheral seal 20a on rear bearing 19a provides redundant means to block backward flow.

Illustrated in FIGS. 20, 25, and 26 is a manual actuation means comprising the slot knob, tang and securement structures for effecting reciprocation of the cup piston along the drive shaft. The knob is sized for thumb actuation and is contoured to the OD of housing 11a.

Following assembly of the piston and drive shaft into the housing, tang 50, protruding from the rear portion of knob 49, is inserted through housing slot 51 to engage, lock and seal against cup slot 50a of outer cylinder 54. Locking and sealing is accomplished by configuring knob tab 56, in the same manner that flanges 45,45a on housing door 29 lock and seal. Tang 50 is sized to provide free longitudinal sliding action of the piston and knob assembly along the housing slot 51. Knob 49 also incorporates retention slot 57 which frictionally engages a rear edge of the housing slot to hold the piston assembly stationary with respect to the housing during shipping and handling.

Assembly of the cup piston is accomplished in the same fashion as in the auger assembly, except the last operation is assembly of knob 49 to the cup piston 52. Initially, slot 51 is temporarily sealed to facilitate filling the housing with dentifrice and bleeding air from the system during piston installation. When drive shaft 16a is positioned such that door 29 can be closed between bearings 25 and 30, lip seals 53 and 55 on piston 52 extend beyond slot 51 and retain dentifrice within the housing chamber. Packaging for storage and shipment is done in the same manner as for prophy angle 10.

In use, prophy angle 10a is attached to the dental hand piece in the same fashion as described above. Clockwise rotation of the drive shaft in turn rotates the right angle drive unit. Piston 52 is prevented from rotating by tang 50 reacting against slot 51 in stationary housing 11a. The rate and volume of dentifrice flow is controlled by the operator pushing forward on knob 49. This causes piston 52 to move dentifrice through passageways in the gear units and into the prophy cup.

Second Embodiment: Reusable Prophy Angles for Dispensing Dentifrice

A second embodiment of this invention adapts externally located dentifrice dispensing mechanisms to reusable prophy angles. The object of this embodiment is to provide a disposable dentifrice attachment that permits controlled flow of dentifrice to the cup without removal of the tool from the patient's mouth. Variations include dentifrice dispensers attached directly to the prophy tool and remote dispensers attached to the tool, each having various means to move the dentifrice.

First Alternative: Dentifrice Dispenser System Attached to Reusable Prophy Angle As shown in FIGS. 27–31, a permanent or reusable prophy angle is indicated generally at 60 and a disposable dentifrice dispenser is indicated at 64. Dentifrice communication from the dispenser into the prophy angle is facilitated by a dispensing head extension 63 above right angle drive unit 17a. Disposable dentifrice dispenser 64 comprises an annular chamber that is installed over reusable prophy angle 60 from the rear, thus engaging chamber connection 69 into port 65 of the dispensing head extension.

Modifications to the reusable prophy angle 60 are best shown in FIGS. 29 and 30. Reusable prophy angles are generally made of metal or other materials intended for multiple usage. Such construction includes a hollow body enclosing an axial drive shaft and a right angle gear drive. In FIGS. 29 and 30, only the body 61 and right angle gear drive 17a require modification to move dentifrice from dispenser 64 into prophy cup 12. Drive shaft 16b remains unchanged from typical commercial models.

In this first alternative, the axial portion of prophy body 61 is sized with a uniform outside diameter to externally accommodate and support disposable dentifrice dispenser 64. The body internal profile is unchanged from typical commercial reusable prophy angles. Body door 29a is attached with a thicker "living hinge" to accommodate the increased wall thickness in the bearing section.

Similar to the door and hinge of the disposable prophy systems, the body door 29a serves a dual purpose. Internal flanges molded in the door protrude into body 61 providing precise juxta positioning between bearings 25 and 30 and shaft drive section 26a. Thus, the door and integral flanges act to position and retain drive shaft 16b in precise location within the body. At the same time, the flanges engage drive gear 33a, which extends from gear bearing 32a, with spur gear 35 on right angle gear unit 17a. This engagement also retains that unit in its precise location upon assembly.

The dispensing head 62 includes an upper extension 63 as shown in FIGS. 29 and 30. The extension includes port 65 facing rearward and a small diameter orifice 66 extending on centerline through the extension pin 34b and intersecting at right angle with port 65. The port 65 functions to engage and seal connections from any external dentifrice sources. If a dentifrice attachment is not used, port 65 may be plugged during operation of the prophy angle.

FIG. 35 shows right angle drive unit 17a, which has an external profile similar to the disposable prophy angle variations. However, the cross-section view in FIG. 36 shows a different internal aperture pattern. Top opening 34c at the upper end of the unit provides for alignment, bearing, and rotational sealing when engaged with housing extension pin 34b of the prophy body. The extension pin incorporates a ring seal of a type commonly used to prevent backward flow of fluids in rotating male/female connection applications (not shown). Center aperture 66a intersects on centerline with top opening 34c to provide unrestricted passage for dentifrice through the right angle drive unit into the prophy cup.

FIGS. 31–34 show the disposable dentifrice dispenser 64 comprised of annular chamber 70 within which interfits ring piston 73. Cap member 75 is used to enclose the annular chamber.

The annular chamber may be an integrally molded structure having a chamber open end 77 and a chamber closed end 78 with connecter 69 outwardly disposed at the upper closed end with connector seal 69a. The chamber structure comprises outer cylinder 67 and inner cylinder 68 having a flat ring closure 72 angularly disposed over the chamber closed end.

Ring piston 73 is cylindrical in shape with a thickness about equal to the radial distance between the inner and outer cylinder walls. The piston seals against each adjacent cylinder wall and moves axially within the annular chamber. Static seals 73a and 73b are incorporated in the OD and ID of the piston as shown in FIG. 32.

Cap member 75 is sized to press fit into the open end 77 of the annular chamber after dentifrice is injected and ring piston 73 is installed. The cap member includes a central opening 79 to permit the connector end of prophy body 61 to extend therethrough as shown in FIG. 27. The cap member also includes a connector opening 76 used to connect with a source of low pressure air for moving the cap member axially against the dentifrice. The air source may be from dental office air supply, from a mechanical pump, pressurized canister or from a syringe or thumb pump.

Assembly of the disposable dentifrice dispenser involves injecting dentifrice into the annular cavity through chamber open end 77 until the dentifrice flows out of chamber connector 69. The chamber connector is then plugged and the remainder of the chamber is filled with dentifrice while air is bled from the open end 77. Connector 69 is unplugged when ring piston 73 is inserted into the annular chamber permitting any excess air and dentifrice to exit. Cap member 75 is then pressed into the chamber open end until seated to complete the assembly. Chamber connector 69 is capped and port 65 is plugged for shipping. The disposable dispenser is packaged in the same manner as previously above.

In operation, the disposable dispenser 64 is slipped over the outside of reusable prophy angle body 61 from the rear connector end until chamber connector 69 engages port 65 in the dispensing head extension 63. The dispenser is retained in proper location by positioning tab 71 on the inside wall of inner cylinder 68. The tab engages detent 71a on the outer wall of body 61. The overall assembly is then mounted on the sheath of dental hand piece 13 and the collet is locked on drive shaft 16b.

An external pressurized air source (not shown) is coupled to connector opening 76 in cap member 75. Upon actuation of the pressurized source, ring piston 73 will exert pressure against the dentifrice and cause its movement through the dispensing head and into the prophy cup. During prophylaxis, air is actuated when needed to replenish the dentifrice supply in the cup. After prophylaxis, the depleted dispenser 64 is removed from the prophy body 61 and safely discarded. The prophy angle 60 is autoclaved, or otherwise cleaned and sterilized, for reuse.

Second Alternative: Remote Dentifrice Supply, Reduced Profile Reusable Prophy Angle Although a dentifrice dispenser coupled to a reusable prophy angle has attractive features, some operators may prefer a prophy tool that is smaller in dimension to use inside a patient's mouth. The following alternative provides a reduced profile prophy angle having a dispensing head port for connection to a dentifrice conduit, but the supply of dentifrice will be remote from the prophy angle. Note that in this alternative, the dentifrice conduit may be detachable from the prophy angle and discarded after use.

As shown in FIGS. 37–39, a small profile reusable prophy angle is indicated generally at 80 and a dentifrice conduit is indicated at 90. Dentifrice communication from the conduit through right angle gear unit 17a into prophy cup 12 is facilitated by engaging male connector 95 into female port 65a of the dispensing head.

In this alternative, the modified body 81 has a reduced diameter which merges into a tapered section 82 which is followed by a bearing section 83. The dispensing head section 84 includes an enlarged crown portion 85. The internal profile of the modified body is similar to the prophy body previously described and includes door 29 attached by a living hinge with interacting flanges. As before, the flanges engage the inner faces of inner bearing 25 and mid-bearing 30 to properly juxtapose modified drive gear 33a with a modified spur gear (not shown) in right angle gear unit 17a. Drive shaft 16b remains unchanged from typical commercial models.

The head crown 85 incorporates female port 65a intersecting at right angle with elongated aperture 66b extending on centerline through housing extension pin 34b and drive unit 17a. The purpose of port 65a is to engage and seal a male connection from any external dentifrice source. If a remote dentifrice supply is not used, port 65 may be plugged.

Right angle drive unit 17a has an external profile similar to the previously described disposable prophy angles. Top opening 34c in said drive unit provides for alignment, bearing, and rotational sealing when engaged with housing extension pin 34b. The extension pin incorporates a seal member 86 to prevent backward flow of fluids into the gear units.

FIG. 40 shows dentifrice conduit 90 made of a material compatible with the material of modified body 81. The conduit may be molded into the shape shown in FIG. 40 or be flexed into such shape. It includes a raised section 91 that conforms to reduced diameter body 81. The raised section inclines into lower section 92 that conforms to both of the tapered section 82 and bearing section 83. The conduit inclines upwardly from the lower section to raised end section 93 that is aligned with female port 65a. The raised end section terminates at male connector 95 which incorporates a static seal 95a and an abutment flange 94.

The opposite end of the conduit connects by flexible tubing or an equivalent, to a disposable dentifrice source (not shown) positioned at a location convenient to the operator. The dentifrice source may be manually, mechanically or air actuated and may be attached to the dental hand piece, to the operator, or to an adjacent item of equipment such as a dental tray.

FIGS. 41 and 42 show clip 96, made of spring-type flat stock material and permanently formed into a caliper shape having an upper smaller portion 97 and a lower larger portion 98. Upon installation, the smaller portion conforms to lower section 92 of the conduit and the larger portion 98 conforms to the outside diameter of bearing section 83. The combination of clip force and contour of the conduit reacting on the tapered section 82 effectively maintains engagement of male connection 95 with female port 65 without need for other latching mechanisms.

Reusable prophy angle 80 is assembled in the same manner as disposable prophy angle 10 in FIG. 1. Right angle drive unit 17a is inserted into head section 84. Then, drive shaft 16b is inserted into modified body 81 until bearings 25 and 30 are positioned such that door 29 can be closed and locked. Male connector 95 of the conduit 90 is inserted and sealed into female port 65a and is secured in place using clip 96.

The opposing end of the conduit is connected to the dentifrice source by tube means or the like located in a position convenient to the operator. Dentifrice is moved under operator control from the remote source through conduit 90, female port 65a and elongated aperture 66b to fill the inside of prophy cup 12. The cup is refilled as needed by the operator during prophylaxis without removal of the prophy angle from the patient's mouth. Optionally, the prophy cup may include a one-way valve.

While the invention has been described with respect to preferred embodiments, it will be clear to those skilled in the art that modifications and improvements may be made to the invention without departing from the spirit and scope of the invention. Therefore, the invention is not to be limited by the specific illustrative embodiments, but only by the scope of the appended claims.

We claim:

1. An implement having a moving tool part which utilizes a flowable material for cleaning, bleaching, polishing or abrading a workpiece comprising:

an elongated housing having a wall structure that defines an open interior terminating at a connector end and an opposing dispenser end, said housing including a storage area for said flowable material in communication with said dispenser end;

a gear train positioned in said dispenser end, said gear train being connected to said tool part which is outside said dispenser end;

a drive shaft having a drive gear section inside said dispenser end connected to said gear train, said drive shaft extending from said gear train through said housing to a free end which is adapted for connection to an external power source;

a passageway in said dispenser end interconnecting said storage area with said tool part, said tool part having a body portion with an aperture in communication with said passageway, said aperture including a one-way valve means for preventing backward flow of contaminants into said passageway; and, displacement means operatively connected to said storage area for moving flowable material from said storage area through said passageway to said tool part.

2. The implement of claim 1 wherein said storage area is within said housing open interior and said drive shaft rotates within said storage area, said displacement means comprising a baffle extending into said storage area radially from a spiral curve along the longitudinal axis of said drive shaft.

3. The implement of claim 1 wherein said displacement means comprises a piston in said storage area having a manual actuating means for causing movement of said piston.

4. The implement of claim 1 wherein said displacement means comprises a piston in said storage area having a pneumatic actuating means for causing movement of said piston.

5. In a tooth cleaning device having a body with a dispensing head from which extends a rotatable dentifrice holding means for applying a dentifrice preparation to one's teeth where in the improvement comprises:

said dentifrice holding means comprising a cup body having a dentifrice outlet within which is a one-way valve means for preventing backward flow of contaminants into said outlet.

6. A tooth cleaning implement comprising:

a tubular housing having a first open end and an opposing second end;

a chamber within said housing containing a flowable dentifrice preparation;

a drive shaft positioned within said housing having a connector end proximate said first open end and a drive end proximate said second end;

said second end containing a gear unit in engagement with said drive end having a passage in communication with said chamber;

a prophy cup having a cup body with a dispensing outlet in communication with said passage, said outlet including a one-way valve means for preventing backflow into said outlet; and, transport means connected to said drive shaft for moving said dentifrice preparation from said chamber to said dispensing outlet.

7. The implement of claim 6 wherein said transport means comprises a continuous spiral baffle extending into chambers radially outward from said drive shaft.

8. The implement of claim 6 wherein said drive end includes bearing means for rotational support of said drive shaft within said housing.

* * * * *